US011194829B2

(12) United States Patent
Dennis et al.

(10) Patent No.: US 11,194,829 B2
(45) Date of Patent: Dec. 7, 2021

(54) METHODS AND SYSTEM FOR ENTITY MATCHING

(71) Applicant: Experian Health, Inc., Franklin, TN (US)

(72) Inventors: John Dennis, Marietta, GA (US); Sean Daniel Reisz, Tucker, GA (US)

(73) Assignee: Experian Health, Inc., Franklin, TN (US)

(*) Notice: Subject to any disclaimer, the term of this patent is extended or adjusted under 35 U.S.C. 154(b) by 910 days.

(21) Appl. No.: 15/468,600

(22) Filed: Mar. 24, 2017

(65) Prior Publication Data
US 2018/0276312 A1 Sep. 27, 2018

(51) Int. Cl.
G06F 16/25 (2019.01)
G16H 10/60 (2018.01)

(52) U.S. Cl.
CPC ............. *G06F 16/25* (2019.01); *G16H 10/60* (2018.01)

(58) Field of Classification Search
None
See application file for complete search history.

(56) References Cited

U.S. PATENT DOCUMENTS

| 5,786,998 | A  | 7/1998  | Neeson et al.     |
|-----------|----|---------|-------------------|
| 6,968,348 | B1 | 11/2005 | Carone et al.     |
| 7,720,846 | B1 | 5/2010  | Bayliss           |
| 8,122,061 | B1 | 2/2012  | Guinness          |
| 8,286,085 | B1 | 10/2012 | Denise            |
| 8,332,366 | B2 | 12/2012 | Schumacher et al. |
| 8,438,184 | B1 | 5/2013  | Wang              |
| 8,495,384 | B1 | 7/2013  | DeLuccia          |
| 8,577,849 | B2 | 11/2013 | Yakout et al.     |
| 8,583,684 | B1 | 11/2013 | Kirmse            |
| 8,965,848 | B2 | 2/2015  | Caceres           |

(Continued)

OTHER PUBLICATIONS

Varpa et al., Genetic Algorithm Based Approach in Attribute Weighting for a Medical Data Set Sep. 3, 2014, Journal of Computational Medicine, vol. 2014, http://downloads.hindawi.com/archive/2014/526801.pdf.*

(Continued)

*Primary Examiner* — Jason G Liao
(74) *Attorney, Agent, or Firm* — Knobbe, Martens, Olson & Bear, LLP

(57) ABSTRACT

Entity matching is provided. A request to determine a second entity matching with a first entity may be received. Demographic fields to be compared to determine the match may be determined. Comparison weights including an agreement weight, a disagreement weight, and a null weight may be assigned to each of the plurality of demographic fields. The received request may be parsed to determine demographic fields data related to the second entity. The demographic fields data may be compared with indexed demographic data which may include a plurality of records. The demographic fields data may be compared for the determined plurality of demographic fields. A comparison weight for each of the plurality of demographic fields may be determined based on the comparison. The first entity matching with the second entity may be determined from the indexed demographic data based on determined comparison weights for the plurality of demographic fields.

20 Claims, 5 Drawing Sheets

(56) References Cited

U.S. PATENT DOCUMENTS

| | | |
|---|---|---|
| 9,002,883 B1 | 4/2015 | Kirmse |
| 9,436,704 B2 | 9/2016 | Gershon et al. |
| 9,589,058 B2 | 3/2017 | Balduzzi et al. |
| 9,785,696 B1 | 10/2017 | Yakhnenko et al. |
| 9,864,746 B2 | 1/2018 | Gilder et al. |
| 9,946,699 B1 | 4/2018 | Dye et al. |
| 9,953,047 B2 | 4/2018 | Lambert et al. |
| 10,102,259 B2 | 10/2018 | Agrawal et al. |
| 10,275,828 B2 | 4/2019 | Reisz et al. |
| 10,430,428 B2 | 10/2019 | Ott et al. |
| 10,783,137 B2 | 9/2020 | Katz |
| 10,817,966 B2 | 10/2020 | Dennis et al. |
| 2003/0063072 A1 | 4/2003 | Brandenberg et al. |
| 2003/0120652 A1 | 6/2003 | Tifft |
| 2005/0038772 A1 | 2/2005 | Colrain |
| 2005/0147947 A1 | 7/2005 | Cookson, Jr. et al. |
| 2006/0026156 A1 | 2/2006 | Zuleba |
| 2007/0266037 A1 | 11/2007 | Terry et al. |
| 2007/0299697 A1* | 12/2007 | Friedlander ............ G06Q 10/00 705/3 |
| 2008/0120129 A1 | 5/2008 | Seubert et al. |
| 2008/0126335 A1 | 5/2008 | Gandhi et al. |
| 2008/0183693 A1* | 7/2008 | Arasu ................. G06F 16/2458 |
| 2008/0244008 A1 | 10/2008 | Wilkinson et al. |
| 2008/0270363 A1 | 10/2008 | Hunt et al. |
| 2009/0024623 A1 | 1/2009 | Broder et al. |
| 2009/0106242 A1 | 4/2009 | McGrew et al. |
| 2010/0049695 A2 | 2/2010 | Morsa |
| 2010/0175024 A1 | 7/2010 | Schumacher et al. |
| 2011/0106617 A1 | 5/2011 | Cooper |
| 2011/0179011 A1 | 7/2011 | Cardno et al. |
| 2012/0215768 A1 | 8/2012 | Zellweger |
| 2012/0226889 A1 | 9/2012 | Merriman et al. |
| 2012/0290950 A1 | 11/2012 | Rapaport et al. |
| 2012/0302268 A1 | 11/2012 | Casto et al. |
| 2013/0054274 A1 | 2/2013 | Katyal |
| 2013/0054570 A1 | 2/2013 | Gonzales et al. |
| 2013/0073449 A1 | 3/2013 | Voynow et al. |
| 2013/0080192 A1 | 3/2013 | Bucur et al. |
| 2013/0288647 A1 | 10/2013 | Turgeman |
| 2013/0339314 A1 | 12/2013 | Carpentier et al. |
| 2014/0039929 A1 | 2/2014 | Vdovjak et al. |
| 2014/0040274 A1 | 2/2014 | Aravamudan et al. |
| 2014/0236572 A1 | 8/2014 | Meshulam et al. |
| 2014/0372458 A1 | 12/2014 | Jurca |
| 2014/0379374 A1 | 12/2014 | Vinals |
| 2015/0026153 A1 | 1/2015 | Gupta et al. |
| 2015/0262246 A1 | 9/2015 | Stack et al. |
| 2015/0286747 A1 | 10/2015 | Anastasakos et al. |
| 2015/0356142 A1 | 12/2015 | Proux |
| 2015/0363449 A1 | 12/2015 | Lambert et al. |
| 2016/0037197 A1 | 2/2016 | Kitts et al. |
| 2016/0055142 A1 | 2/2016 | Strassner |
| 2016/0132605 A1 | 5/2016 | Jiang |
| 2016/0171027 A1 | 6/2016 | Agrawal et al. |
| 2016/0267115 A1 | 9/2016 | Pletcher et al. |
| 2016/0283520 A1 | 9/2016 | Yamaji et al. |
| 2016/0283548 A1 | 9/2016 | Han et al. |
| 2016/0335341 A1 | 11/2016 | Krauss |
| 2017/0053002 A1 | 2/2017 | Bowman et al. |
| 2017/0111372 A1 | 4/2017 | Jamaa |
| 2017/0132234 A1 | 5/2017 | Mehta |
| 2017/0147650 A1 | 5/2017 | Hattori et al. |
| 2017/0169168 A1 | 6/2017 | Batchelor et al. |
| 2018/0102936 A1 | 4/2018 | Curtis |
| 2019/0303371 A1 | 10/2019 | Rowe et al. |
| 2021/0064681 A1 | 3/2021 | McGrath et al. |

OTHER PUBLICATIONS

Talbot et al., Entity Information Life Cycle Big Data 2015, Elsevier, 1st ed., pp. 1-235.*

Jafari et al., Expert Pruning Based on Generic Algorithm in Regression Problems.*

Zhou et al., Ensembling neural networks: Many could be better than all May 2, vol. 137, p. 239-63.*

* cited by examiner

METHODS AND SYSTEM FOR ENTITY MATCHING

BACKGROUND

Several industries use various entity matching technologies to uniquely identify entities. For example, health care providers match patient records to identify previous or similar records. However, when a person moves or changes a last name (e.g., due to marriage or divorce), for example, it becomes challenging to link those two "people" together and confirm that they are one person. In previous systems, social security numbers or other governmental identification numbers have helped in creating confidence in whether two entities with different demographic data are, in fact, one entity, but these identifiers are not always reliable, and the availability of some identifiers in records, such as, social security numbers, has decreased due to security and privacy concerns. Additionally, data entry errors add to the challenge, as entered identifiers may include typographical errors and therefore cannot be relied upon.

SUMMARY

This summary is provided to introduce a selection of concepts in a simplified form that are further described below in the Detailed Description section. This summary is not intended to identify key features or essential features of the claimed subject matter, nor is it intended as an aid in determining the scope of the claimed subject matter.

Aspects of methods and systems for entity matching are provided herein. A request to determine a second entity matching with a first entity may be received. A plurality of demographic fields to be compared to determine the match may be determined. Comparison weights including an agreement weight, a disagreement weight, and a null behavior may be assigned to each of the plurality of demographic fields. The received request may be parsed to determine demographic fields data related to the second entity. The demographic fields data may be compared with indexed demographic data which may include a plurality of records each having demographic fields data. The demographics fields data corresponding to the determined plurality of demographic fields may be compared. A comparison weight for each of the plurality of demographic fields may be determined based on the comparison. Determined comparison weights may be aggregated to determine the first entity matching with the second entity.

Examples are implemented as a computer process, a computing system, or as an article of manufacture such as a device, computer program product, or computer readable medium. According to an aspect, the computer program product is a computer storage medium readable by a computer system and encoding a computer program of instructions for executing a computer process.

The details of one or more aspects are set forth in the accompanying drawings and description below. Other features and advantages will be apparent from a reading of the following detailed description and a review of the associated drawings. It is to be understood that the following detailed description is explanatory only and is not restrictive of the claims.

BRIEF DESCRIPTION OF THE DRAWINGS

Further features, aspects, and advantages of the disclosure represented by the examples described in the present disclosure will become better understood by reference to the following detailed description, appended claims, and accompanying Figures, wherein elements are not to scale so as to more clearly show the details, wherein like reference numbers indicate like elements throughout the several views, and wherein:

DETAILED DESCRIPTION

Figure 1:
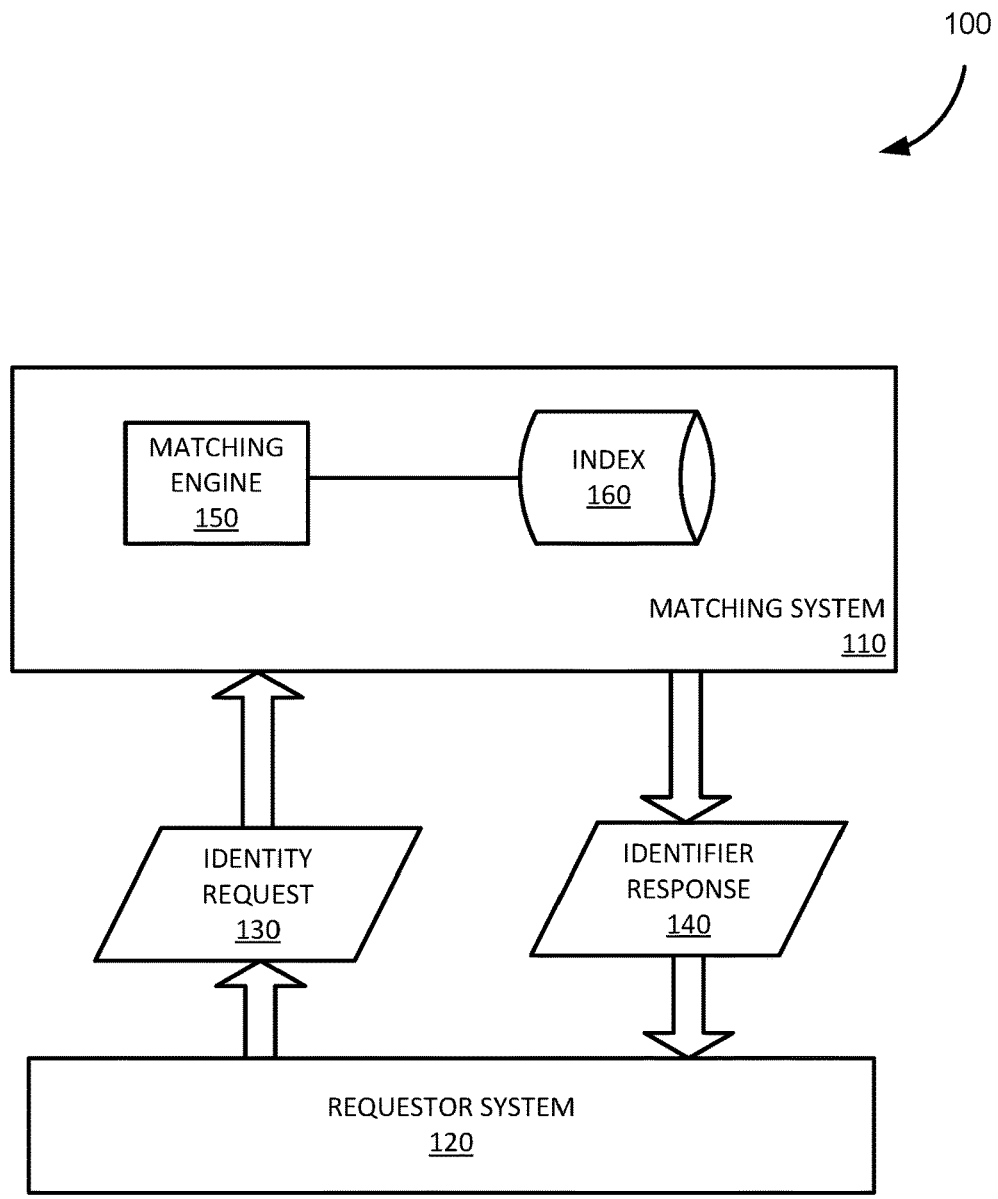
FIG. 1 illustrates an example operating environment in which entity matching may be performed.

Aspects of methods and systems for entity matching are provided herein. For example, two records may be compared to determine if they are related to a same entity. During the comparison of the records, demographic fields data associated to the two records may be compared. Based on how similar the demographic fields data for the two records are, an agreement weight or a disagreement weight may be assigned to the comparison. Comparison weights for each of the demographic fields may be added together. If the added comparison weight is over a certain threshold, the two records may be considered to be representing the same entity.

Before comparison, demographic fields to be compared may be selected. Comparison weights may be assigned to the selected demographic fields. Comparison weights may include an agreement weight, a disagreement weight, and a null weight. During the comparison, data corresponding to each of the selected demographic fields for the two records may be compared. Based on a level of match between the data, a comparison weight is determined for each of the demographic fields. For example, the comparison weight may be determined to be the agreement weight when the data matches, the disagreement weight when the data does not match, and the null weight when the data for a field is missing from either one or both of the two records.

Determining the comparison weights correctly may be essential for providing good record matching. For example, increasing the agreement weight on a date of birth field too much may cause records with the same or similar date of births to be related to a same person despite having a different first name, last name, address, etc. Given a large number of demographic fields and an interrelation between these fields, determining a good set of comparison weights may reduce processing hardware requirements and processing time by a significant amount.

According to an aspect, a method to determine the comparison weights in a rapid manner is disclosed. For example, the disclosed method may provide a list of matching scenarios having at least two records. Each matching scenario may describe which demographic fields of the two records match, which demographic fields do not match, and whether the two records represent a same entity or not. The method may then create a first population of a set of comparison weights which may be randomly chosen within a range. Each member of the first population may be applied against the matching scenarios. Then each member of the population may be judged for its fitness, that is, how well each member performed in providing matches in the matching scenarios. A member with more scenarios that should have been matched having total weights greater than scenarios that should not have been matched may be considered better, or more fit, than a member with more scenarios that should not have matched having total weights greater than scenarios that should have matched.

A predetermined fraction of the first population of weights may be selected based on the fitness. Members of the selected fraction may then be randomly paired with another member of the fraction. Each pair may create a predetermined number of new members by randomly choosing the weights and null behavior from one of the two members of the pair. Moreover, the weights or null behavior may randomly be mutated, that is, set to a value different from either parent. In this way, a new generation of members may be created. This process may be repeated for a given number of generations. A most fit member from any generation may be saved and reported at the end of the process. In this way, the disclosed method may determine a good initial set of weights quickly and efficiently.

FIG. 1 illustrates an example operating environment 100 in which entity matching may be performed. System 100 may include a matching system 110 and a requestor system 120. Matching system 110 may communicate with requestor system 120 to provide a requesting entity that has sent an identity request 130 for an entity with an identifier response 140 which may include a unique identifier for that entity with improved accuracy and reliability in the matching process.

Figure 5:
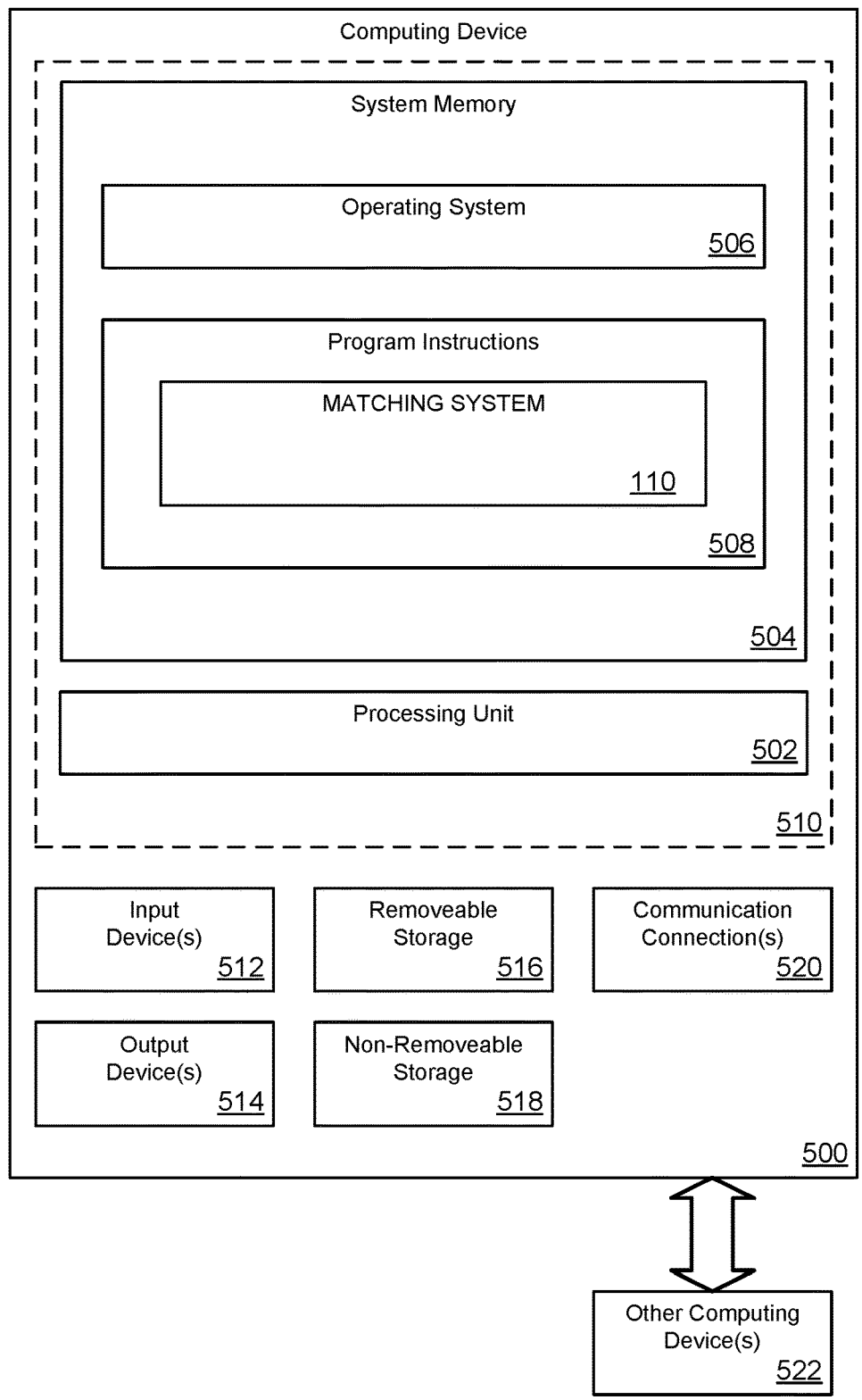
FIG. 5 is a block diagram illustrating example physical components of a computing device with which aspects of the system may be practiced.

Matching system 110 and requestor system 120 are illustrative of a wide variety of computing devices, the hardware of which is discussed in greater detail in regard to FIG. 5. The computing devices may include, but are not limited to: servers, desktop computers, laptops computers, tablets, smart phones, personal digital assistants, and distributed systems that are run on multiple computing devices. In various aspects, matching system 110 and requestor system 120 may communicate with one another via the Internet, a private network, or a virtual private network or tunnel over a public network, which may include wired and wireless components to link systems that are located remotely from each other.

Matching system 110 may be operable to receive identity requests 130 from requestor systems 120 that are remote or local to the computing environment in which matching system 110 is operated. Identity requests 130 may include several fields of demographic data, which may include more or fewer fields than are present in the demographic data sources available to matching system 110 or may be unreliable (e.g., due to human entry errors). For example, a requestor who submits the identity request 130 may not include a demographic field for an entity's address, whereas the matching system 110 may maintain or has access to demographic data related to the entity's address. Similarly, a requestor may include a demographic field in identity request 130 (e.g., height, weight, eye color, schools attended, customer number) for which matching system 110 may not maintain or have access to.

Matching engine 150 may determine a plurality of demographic fields to be used to determine a match. For example, matching engine 150 may select a plurality of demographic fields which may be compared to determine the match. In addition, matching engine 150 may assign comparison weights to each the plurality of demographic fields. Matching engine 150 may determine the comparison weights using an iterative method. An example, one method for determining the comparison weights is described with reference to FIG. 2 of the specification.

In one aspect, matching engine 150 may determine matches between records based on matching data corresponding to the plurality of demographic fields for the records. For example, matching engine 150 may determine a comparison weight for each of the plurality of demographic data fields based on a match in corresponding records. Matching engine 150 may aggregate the comparison weights for each of the plurality of demographic fields and compare it with a confidence threshold to determine the match.

Various aspects allow for various confidences to be determined between two sets of records as to whether they refer to the same entity. For example, two systems that receive an identity request 130 with demographic data for "John" "Doe" "123 Main Street" "Born: Jan. 1, 1950" may match the entity described in the identity request 130 to an entity for "Johnathan" "Doe" "122 Main Street" "Born: Jan. 1, 1950" and "John" "Roe" "123 Main Street" "Born: Jan. 2, 1950" respectively based on different weights assigned to different fields when comparing the demographic data.

In aspects where more than one entity satisfies the confidence threshold, the candidate entity with the highest confidence score may be selected as the match. In various aspects, identifier response 140 may include the unique identifier for the entity whose identifier was requested in identity request 130, as well as other information to allow the requestor to correlate an identifier response 140 to the identity request 130 that initiated the entity matching.

Figure 2:
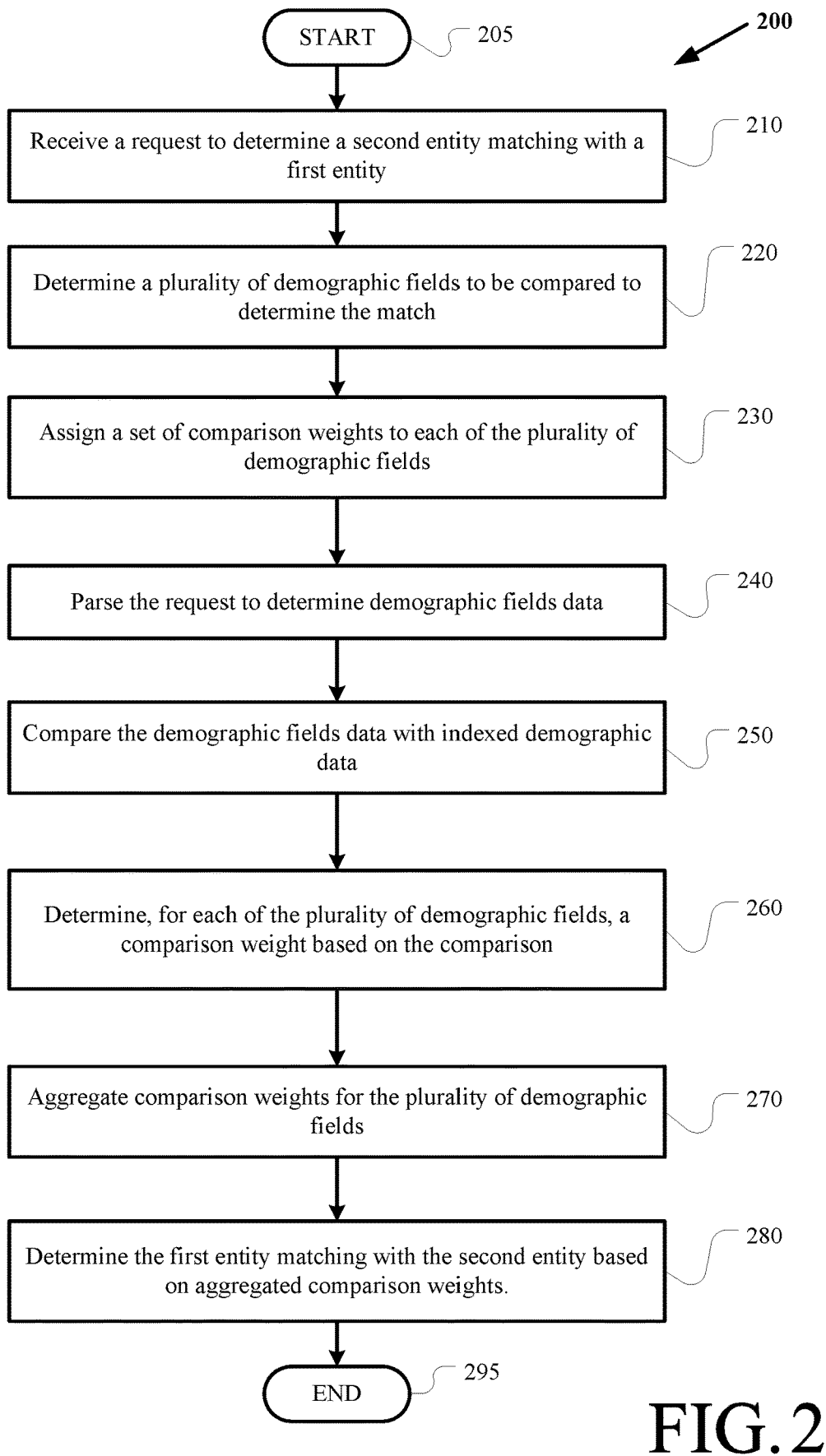
FIG. 2 is a flow chart showing general stages involved in an example method for determining matching entity.

FIG. 2 is a flow chart showing general stages involved in an example method 200 for determining a matching entity. Method 200 may begin at start OPERATION 205 and proceed to OPERATION 210, where a request to determine a second entity matching with a first entity may be received. In one aspect the request may be received to determine an identifier associated with a record or an entity. In another aspect, the request may be received to determine whether two given records match with each other. In yet another aspect, the request may be received to determine whether two given records belong to one entity or two separate entities. In yet another aspect, the request may be received to determine where there is some relationship between two entities of records. For example, the request may be received to determine whether two records represent records for twins or two entities sharing an address, or date of birth, etc.

After receiving the request at OPERATION 210, method 200 may proceed to OPERATION 220 where a plurality of demographic fields to be compared to determine the match may be determined. For example, a system administrator or matching engine 150 may determine the plurality of demographic fields which may be compared to determine the match. In one aspect, only one demographic field may be compared to determine the match. For example, a social security number field may be selected to be compared between two records to determine the match. In one aspect, one or more demographic fields may be excluded from the comparison. For example, a social security number field may be excluded to exclude discrepancies or errors in recordation of the social security number.

Once having determined the plurality of demographic fields to be compared to determine the match at OPERATION 220, method 200 may proceed to OPERATION 230 where a set of comparison weights may be assigned to each of the plurality of demographic fields. For example, a system administrator or matching engine 150 may assign a set of comparison weights to the demographic fields. The set of comparison weights may include an agreement weight, a disagreement weight, and a null behavior. The agreement weight may correspond to the comparison weight when two demographic fields data match with each other. The disagreement weight may correspond to a comparison weight when the two demographic fields data do not match with each other. The null behavior may correspond to the comparison weight when one or both demographic fields do not have any associated data to compare. The null behavior may include a null weight, that is, the comparison weight when one or both demographic fields do not have any associated data to compare, or a rule to determine a null comparison weight for the null behavior.

In one aspect, the administrator or matching engine 150 may determine the agreement weight, the disagreement weight, and the null behavior. In another aspect, the set of comparison weights including the agreement weight, the disagreement weight, and the null behavior may be determined using an automated method. In yet another aspect, the set of comparison weights may include one, two, or all three of the agreement weight, the disagreement weight, and the null behavior. An example method for determining the set of comparison weights is described with respect to FIG. 3.

After assigning the set of comparison weights to each of the plurality of demographic fields at OPERATION 230, method 200 may proceed to OPERATION 240, where the received request may be parsed to determine demographic fields data. For example, the received request may be parsed to identify the demographic fields data associated with the request or the second entity. The demographic fields data may, for example, include one or more of: first name, last name, middle initial, address, governmental identification number, date of birth, etc. In one aspect, the received request may be parsed to only identify the demographic fields data associated with the predetermined demographic fields to be compared. Hence, instead of parsing the received request to determine all of the demographic fields data, the received request may be parsed to determine the demographic fields data associated with a selected number of demographic fields.

Having parsed the received request at OPERATION 240, method 200 may proceed to OPERATION 250, where the demographic fields data may be compared with indexed demographic data. For example, index 160 may include a plurality of records comprising demographic data. Matching engine 150 may compare the demographic fields data with demographic data in index 160. The comparison may include, for example, comparing the demographic fields data for each of the plurality of demographic fields, determined to be compared, from the received request and indexed demographic data to determine the match. If there is no demographic fields data corresponding to a demographic field, then it may be marked as a null field.

In one aspect, the comparison in method 200 may not be limited to indexed records, and may include comparing the demographic fields data from the request to the demographic fields in Internal and External Demographic data resources. In another aspect, method 200 may compare the demographic fields data from the request to the demographic fields in a preselected record to determine whether the preselected records are associated with a second entity. For example, if two preselected records are being matched, then the demographic fields data corresponding each of the plurality of field determined to be compared to determine the match may be compared for both records.

In one aspect, demographic fields data may be sanitized and standardized before comparing. Sanitization of the demographic field may include deleting known-unreliable record fields. For example, if the value of a social security number for an entity were 000-00-0000, which is recognized as an invalid social security number, it may not be considered to be part of the request; it may be treated as blank or null. In another example, if the value of a first name for an entity were "baby girl", which may be recognized as a placeholder value used by some medical facilities to refer to unnamed newborn girls, it may not be considered to be a part of the request and may not be added to the entity's records as a valid value for the first name field. In various aspects, standardization of the demographic field data may include formatting the demographic fields data to make it consistent with the data stored in index 160. For example, if the value of the address field is "125 N Elm", it may be changed to "125 ELM", wherein the "N" indicating North from the address field is deleted and the case of the street name is standardized to improve consistency between data fields received in different requests or data sources. In another example, the words or abbreviations for street, boulevard, avenue, etc., may also be removed from the address field since they may be entered in a plurality of ways which may increase inconsistency between records. In one aspect, matching engine 150 may sanitize and standardize the demographic fields data.

After comparing the demographic fields data at OPERATION 250, method 200 may proceed to OPERATION 260 where a comparison weight for each of the plurality of demographic fields may be determined. The comparison weight may be determined based on the comparison between the demographic fields data of two records. For example, during the comparison for a demographic field, if the demographic field data matches for the two records, the comparison weight for the demographic field may be determined as the agreement weight assigned to the demographic field. If the demographic field data do not match for the two records, the comparison weight for the demographic field may be determined as the disagreement weight assigned to the demographic field. If there are no demographic field data in either of the two records for the demographic field, the comparison weight for the demographic field may be determined by the null behavior or as a null weight assigned to the demographic field.

After determining comparison weights at OPERATION 260, method 200 may proceed to OPERATION 270, where the comparison weights for the plurality of demographic fields may be aggregated. Aggregation may include simply adding all of the comparison weights, or aggregating each of the agreement weights, the disagreement weights, and null weights separately.

After aggregating the comparison weights at OPERATION 270, method 200 may proceed to OPERATION 280, where a first entity matching with the second entity associated with the request may be identified. For example, the aggregated comparison weights for each of the indexed records may be compared with a predetermined threshold. If the aggregate of the comparison weights for a record is above a predetermined threshold, that record may be considered to be a match with the second entity. An entity associated with the matching record may be considered as the entity matching with the second entity associated with the request. In another aspect, method 200 may identify more than one record matching with the second entity.

In one aspect, method 200 may further provide an identifier associated with the entity. Such identifier may include, for example, a name, an address, or a social security number. If there are more than one records matching with the second entity, method 200 may provide identifiers associated with each of the multiple matching records. Such listing of identifiers may be sorted in a descending or ascending order of aggregated comparison weights. Once the matching entity is identified at OPERATION 280, method 200 may end at OPERATION 295.

Figure 3:
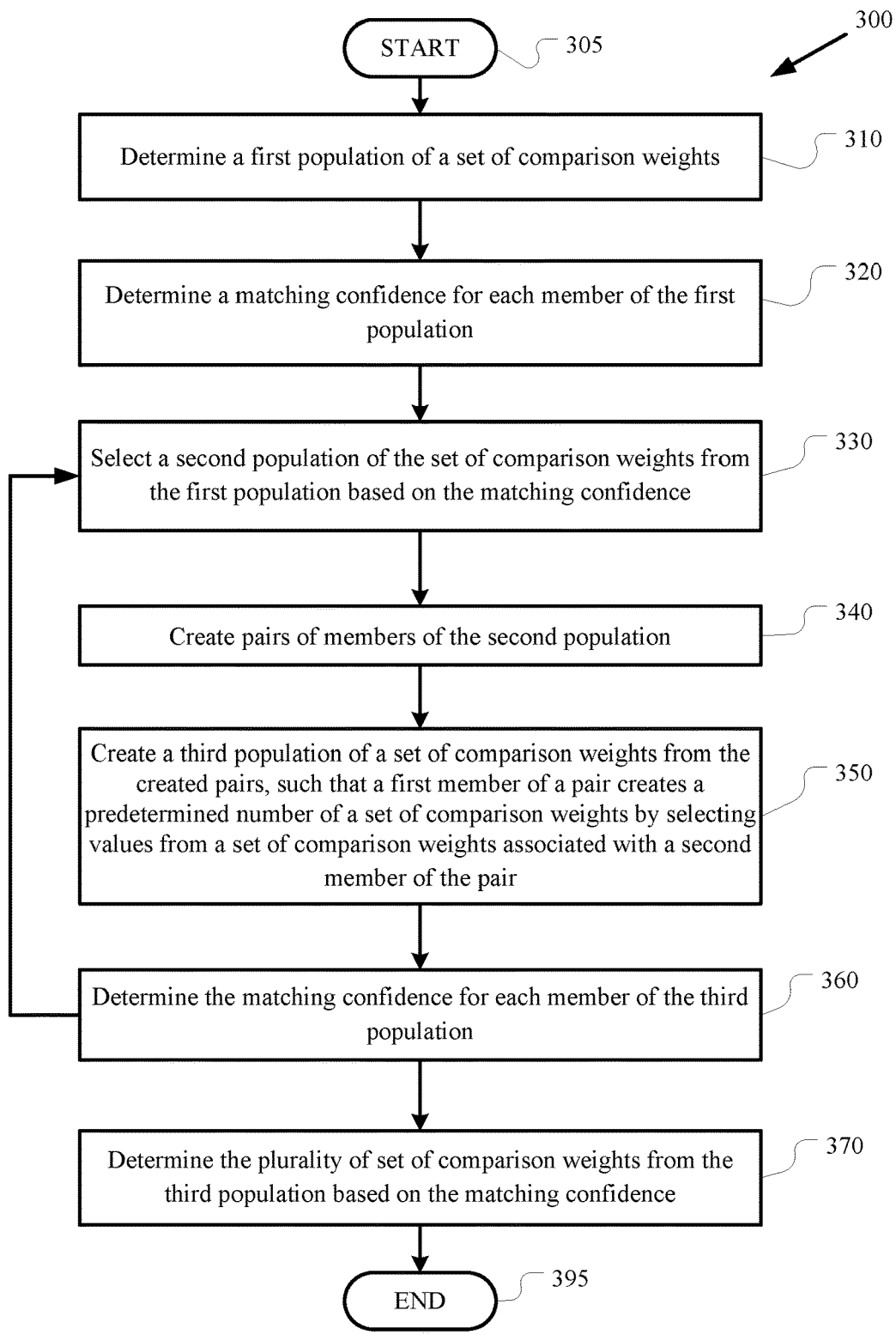
FIG. 3 is a flow chart showing general stages involved in an example method for determining comparison weights for determining the matching entity.

FIG. 3 is a flow diagram illustrating steps of a method 300 for determining a plurality of set of plurality of comparison weights to be assigned to a plurality of demographic fields for entity matching. Method 300 may begin at start OPERATION 305 and may proceed to OPERATION 310, where a first population of the set of comparison weights may be determined. In one aspect, the first population of the set of comparison weights may be randomly selected from a larger available population or may be randomly generated within a predetermined range. For example, the agreement weight and the disagreement weights may be randomly selected within the predetermined range. Null behaviors may be randomly chosen from a set of predetermined behaviors. For example, a gender field may be allowed to have a random behavior, but a social security number field may be forced to behave in a certain way when one or both records social security numbers is not provided.

After determining the first population of the set of comparison weights at OPERATION 310, method 300 may proceed to OPERATION 320, where a matching confidence for each set of comparison weights of the first population may be determined. For example, each member of the first population may use its set of comparison weights against a set of predetermined scenarios. Each member of the first population may be judged for its fitness, that is, how well each member did in providing quality matches given the scenarios. A member with more scenarios that should have been matched having total weights greater than the scenarios that should not have been matched may be considered better or more fit than a member with more scenarios that should not have matched having total weights greater than the scenarios that should have been matched. A method of determine the matching confidence is disclosed in greater detail with respect to FIG. 4.

After determining the first population of the set of comparison weights at OPERATION 310, method 300 may proceed to OPERATION 320 where a second population of the set of comparison weights may be selected from the first population based on the determined matching confidence or fitness. For example, the members of the first population may be sorted based on the matching confidence, and a predetermined fraction of the first population may be selected form the sorted list. In one aspect, the matching confidence for each member of the first population may be compared with a first threshold. The first threshold may be predetermined by a system administrator or matching engine 150. A second population of the set of comparison weights may be selected from the first population based on the comparison. For example, a fraction of the members of first population having the matching confidence higher than the first threshold may be selected as a part of the second population.

After selecting the second population at OPERATION 330, method 300 may proceed to OPERATION 340, where the members of the second population may be paired up. For example, the members of the second population may be randomly paired up with another member. After pairing the members of the second population at OPERATION 340, method 300 may proceed to OPERATION 350, where a third population of the set of comparison weights may be created from the created pairs. For example, a first member of a pair may create a predetermined number of new set of comparison weights by selecting values from the set of comparison weights associated with a second member of the pair. Hence, each pair may create between two and six new sets of comparison weights. For example, each pair may create four new members by randomly choosing the weights and null behaviors from other member pair. In another example, each pair may create six new members by randomly choosing the agreement weight, the disagreement weight, and null behaviors from other member pair.

After creating the third population at OPERATION 350, method 300 may proceed to OPERATION 360, where the matching confidence for each member of the third population may be determined. For example, as discussed above, to determine the matching confidence, each member of the third population may use its set of comparison weights against a set of predetermined scenarios. Each member then may be judged for its fitness, that is, how well each member did in providing quality matches given the scenarios. In one aspect, one or more weights and or the null behaviors of the third population may randomly be mutated, that is, set to a value different from either parent. In this way a new generation of members may be created. In another aspect, OPERATIONS 330-360 may be repeated multiple times or a predetermined number of times creating new generations of the set of comparison weights. In another aspect, the most fit member from any generation may be saved, and reported at the end of method 300.

After determining the matching confidence at OPERATION 360, method 300 may proceed to OPERATION 370, where the plurality of sets of comparison weights may be determined. For example, the plurality of sets of comparison weights may be determined from the third population based on the matching confidence of the members. For example, the matching confidence of the each member of the third population may be compared with a predetermined threshold. Members with the matching confidence higher than the predetermined threshold may be selected as the plurality of sets of comparison weights. In another example, members of the third population may be sorted based on the matching confidence, and a top predetermined fraction of the sorted members may be selected as the plurality of sets of comparison weights. After selecting the plurality of set of comparison weights at OPERATION 370, method 300 may end at OPERATION 395.

Figure 4:
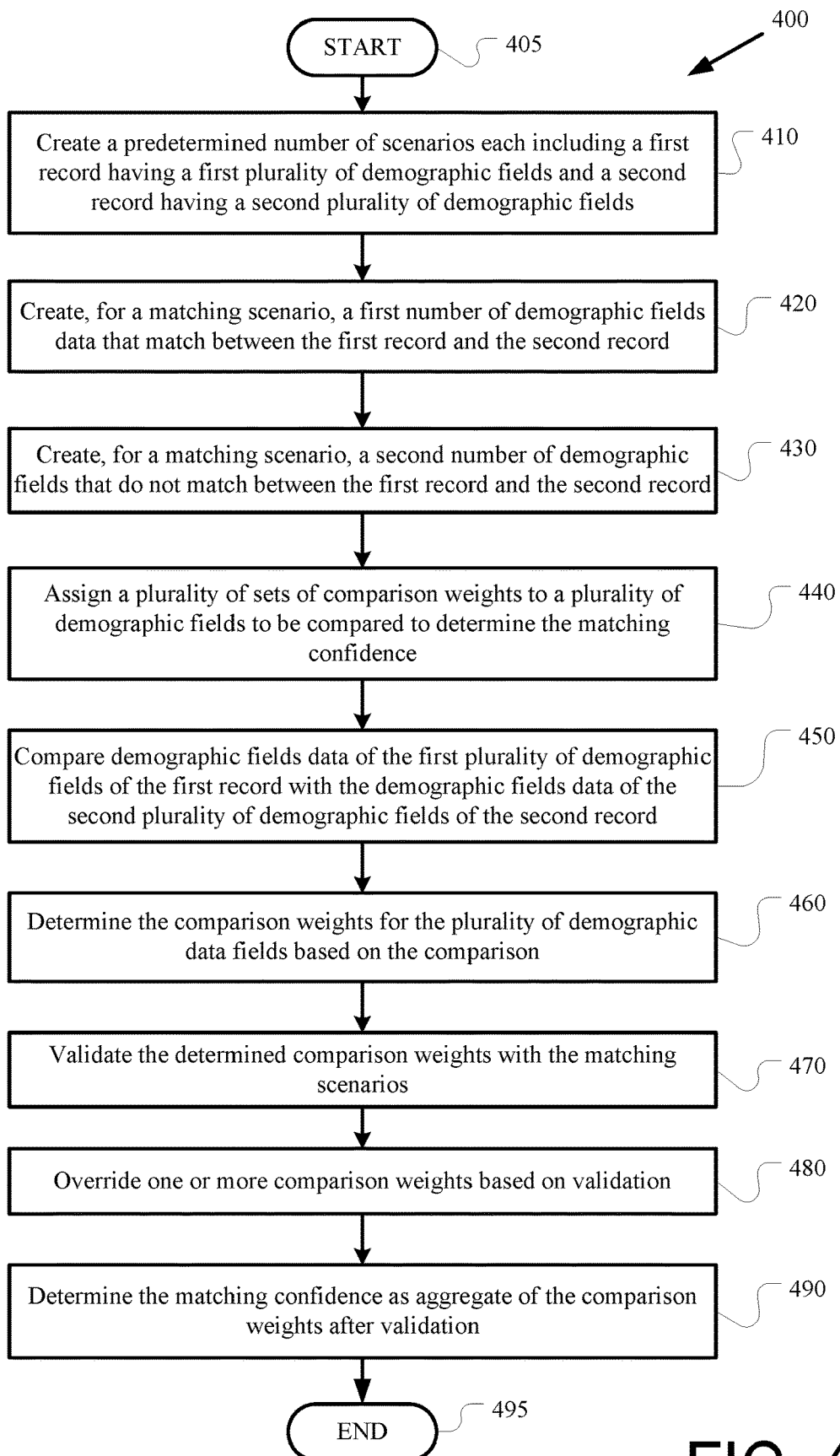
FIG. 4 is a flow chart showing general stages involved in an example method for determining matching confidence for the comparison weights.

FIG. 4 is a flow chart showing steps of a method 400 for determining the matching confidence of a set of comparison weights. Method 400 may begin at start OPERATION 405 and proceed to OPERATION 410 where a predetermined number of matching scenarios may be created. Each matching scenario may include a first record having a first plurality of demographic fields and a second record having a second plurality of demographic fields. In one aspect, a number of the matching scenarios, the first plurality of demographic fields, or the second plurality of demographic fields may be predetermined by a system administrator. In one aspect, there may be more than two records in a matching scenario. In one aspect, a record of a matching scenario may include only one demographic field. In one aspect, the matching scenarios may be created beforehand, and be used to determine the matching confidence. In yet another aspect, the matching scenarios may be labeled based on a matching number of demographic fields. For example, if a matching scenario contains two records for two entities born on same date to the same parents, they may be labeled as twins.

Similarly, if a matching scenario contains two records for two entities living at a same address, they may be labeled as related.

After creating the matching scenarios at OPERATION 410, method 400 may proceed to OPERATION 420 where a first number of demographic fields data that match between the first record and the second record for a matching scenario may be created. For example, the first record and second record may include a predetermined number of demographic fields data which match with each other. In one aspect, the first record and second record of a matching scenario may include all of the demographic fields data matching with each other. In one aspect, the first number of demographic fields data that match between the first record and the second record may be determined by the system administrator. In one aspect, a number of matching scenarios with matching demographic fields data may be determined by the system administrator. In one aspect, each of the demographic fields with matching demographic fields data may be marked for later validation.

After creating the demographic fields that that match between two records of a matching scenario at OPERATION 420, method 400 may proceed to OPERATION 430 where a second number of demographic fields data that do not match between the first record and the second record of a matching scenario may be created. For example, the first record and second record may include a predetermined number of demographic fields data which do not match with each other. In one aspect, the first record and second record of a matching scenario may include all of the demographic fields data not matching with each other. In one aspect, the second number of demographic fields data that do not match between the first record and the second record may be determined by the system administrator. In one aspect, a number of matching scenarios with a predetermined number of demographic fields data not matching may be determined by the system administrator. In one aspect, each of the demographic fields with miss-matching demographic fields data may be labeled for later validation.

After creating the demographic fields that that do not match between two records of a matching scenario at OPERATION 430, method 400 may proceed to OPERATION 440 where a plurality of sets of comparison weights may be assigned to a plurality of demographic fields to be compared to determine the matching confidence. In one aspect, method 400 may use a same plurality of demographic fields used to determine a match between two entities. In another aspect, the plurality of demographic fields to determine the matching confidence may be determined by the system administrator.

After assigning a plurality of sets of comparison weights at OPERATION 440, method 400 may proceed to OPERATION 450 where demographic fields data of the first plurality of demographic fields of the first record may be compared with the demographic fields data of the second plurality of demographic fields of the second record. The demographic field data may be compared for each of the plurality of demographic fields on a field by field basis.

After comparing the demographic fields data at OPERATION 450, method 400 may proceed to OPERATION 460 where comparison weights for the plurality of demographic fields may be determined. For example, for a demographic field of a matching scenario, if the demographic field data matches between a first record and a second record, the comparison weight for the demographic field may be determined to be the agreement weight assigned to the demographic field. If the demographic fields data do not match between the first record and the second record, the comparison weight for the field may be determined to be the disagreement weight assigned to the demographic field. If the demographic field data is not available for either one or both of the first record and the second record, the comparison weight for the demographic field may be determined to be the null weight assigned to the demographic field After determining the comparison weights at OPERATION 460, method 400 may proceed to OPERATION 470, where the determined comparison weights may be validated for the matching scenarios. For example, a demographic field was marked to contain matching data for both a first record and second record of a matching scenario, then the comparison weight should correspond to the agreement weight assigned to the demographic field. Similarly, if the demographic field was marked to contain miss-matching data for both the first record and the second record of the matching scenario, then the comparison weight should correspond to the disagreement weight assigned to the demographic field. Hence, the comparison weights determined at OPERATION 460 may be verified at OPERATION 470 using the marked marching or mismatching demographic fields of the matching scenarios.

In one aspect, even the overall comparison weight of the matching scenarios may be validated. For example, if a matching scenario has all of the demographic fields data matching between the first record and the second record, the aggregate comparison weight for the matching scenario must be greater than a predetermined threshold. Similarly, if a matching scenario has all of the demographic fields data miss-matching between the first record and the second record, the aggregate comparison weight for the matching scenario should be less than a predetermined threshold.

After validating the comparison weights at OPERATION 470, method 400 may proceed to OPERATION 480 where one or more comparison weights may be overridden based on validation. The override may include forcing agreement or disagreement on fields that would not have provided that value otherwise. For example, if there is a miss-match between an expected comparison weight and the determined comparison weight for a demographic field of a matching scenario, the determined comparison result may be overridden to match with the expected comparison result. For example, if, for a matching scenario, a demographic field data is created to match between the first record and the second record, the expected comparison weight for the demographic field will be the agreement weight assigned to the demographic field. If the determined comparison weight is different than this expected comparison weight, the determined comparison weight may be overridden to the agreement weight. Similarly, if, for a matching scenario, a demographic field data is created to miss-match between the first record and the second record, the expected comparison weight for the demographic field will be the disagreement weight assigned to the demographic field. And if the determined comparison weight is different than the expected comparison weight, the determined comparison weight may be overridden to the disagreement weight.

In one aspect, overrides may include transposing demographic field data between different fields of the record. For example, if one record has "John Dennis" and the other record has "Dennis John" in names demographic fields, during the comparison a first name demographic field will miss-match between the two records, and similarly a last name demographic field will also miss-match between the two records. But looking at two records as whole, it may make sense to transpose demographic fields data for the first name and last name for one of these records. Similarly, middle name and last name may be transposed.

After overriding the one or more comparison weights at OPERATION 480, method 400 may proceed to OPERATION 490 where the matching confidence may be determined as an aggregate of the comparison weights after validation. For example, for each of the matching scenarios, the aggregated comparison weights may be used to predict an overall match between two records. If the predicted match conforms to the expected result for the matching scenario, then the matching confidence for that scenario will be considered as a positive confidence. However, if the predicted match does not conform to the expected result for the matching scenario, then the matching confidence for that scenario will be considered as negative confidence. An overall matching confidence may be aggregate of positive and negative confidences for the plurality of matching scenarios. For example, an overall matching confidence may be determined as a ratio of positive confidence and negative confidence. After determining the matching confidence at OPERATION 490, method 400 may end at OPERATION 495.

FIG. 5 is a block diagram illustrating physical components of an example computing device with which aspects may be practiced. Computing device 500 may include at least one processing unit 502 and a system memory 504. System memory 504 may include, but is not limited to, volatile (e.g. random access memory (RAM)), non-volatile (e.g. read-only memory (ROM)), flash memory, or any combination thereof. System memory 504 may include an operating system 506, one or more program instructions 508, and may include sufficient computer-executable instructions for a 1080p system, which when executed, perform functionalities as described herein. Operating system 506, for example, may be suitable for controlling the operation of computing device 500. Furthermore, aspects may be practiced in conjunction with a graphics library, other operating systems, or any other application program and is not limited to any particular application or system. This basic configuration is illustrated by those components within a dashed line 510. Computing device 500 may also include one or more input device(s) 512 (keyboard, mouse, pen, touch input device, etc.) and one or more output device(s) 514 (e.g., display, speakers, a printer, etc.).

Computing device 500 may also include additional data storage devices (removable or non-removable) such as, for example, magnetic disks, optical disks, or tape. Such additional storage is illustrated by a removable storage 516 and a non-removable storage 518. Computing device 500 may also contain a communication connection 520 that may allow computing device 500 to communicate with other computing devices 522, such as over a network in a distributed computing environment, for example, an intranet or the Internet. Communication connection 520 is one example of a communication medium, via which computer-readable transmission media (i.e., signals) may be propagated.

Programming modules may include routines, programs, components, data structures, and other types of structures that may perform particular tasks or that may implement particular abstract data types. Moreover, aspects may be practiced with other computer system configurations, including hand-held devices, multiprocessor systems, microprocessor-based or programmable user electronics, minicomputers, mainframe computers, and the like. Aspects may also be practiced in distributed computing environments where tasks are performed by remote processing devices that are linked through a communications network. In a distributed computing environment, programming modules may be located in both local and remote memory storage devices.

Furthermore, aspects may be practiced in an electrical circuit including discrete electronic elements, packaged or integrated electronic chips containing logic gates, a circuit using a microprocessor, or on a single chip containing electronic elements or microprocessors (e.g., a system-on-a-chip (SoC)). Aspects may also be practiced using other technologies capable of performing logical operations such as, for example, AND, OR, and NOT, including, but not limited to, mechanical, optical, fluidic, and quantum technologies. In addition, aspects may be practiced within a general purpose computer or in any other circuits or systems.

Aspects may be implemented as a computer process (method), a computing system, or as an article of manufacture, such as a computer program product or computer-readable storage medium. The computer program product may be a computer storage medium readable by a computer system and encoding a computer program of instructions for executing a computer process. Accordingly, hardware or software (including firmware, resident software, microcode, etc.) may provide aspects discussed herein. Aspects may take the form of a computer program product on a computer-usable or computer-readable storage medium having computer-usable or computer-readable program code embodied in the medium for use by, or in connection with, an instruction execution system.

Although aspects have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data or computer-executable instructions readable by a computing device. The term computer-readable storage media do not include computer-readable transmission media.

Aspects of the present disclosure may be used in various distributed computing environments where tasks are performed by remote processing devices that are linked through a communications network.

Aspects of the disclosure may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing device 500 or any other computing devices 522, in combination with computing device 500, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with the described aspects.

The description and illustration of one or more aspects provided in this disclosure are intended to provide a thorough and complete disclosure the full scope of the subject matter to those skilled in the art and are not intended to limit or restrict the scope of the disclosure as claimed in any way. The aspects, examples, and details provided in this disclosure are considered sufficient to convey possession and enable those skilled in the art to practice the best mode of the claimed disclosure. Descriptions of structures, resources, operations, and acts considered well-known to those skilled in the art may be brief or omitted to avoid obscuring lesser known or unique aspects of the subject matter of this disclosure. The claimed disclosure should not be construed as being limited to any embodiment, aspects, example, or detail provided in this disclosure unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present disclosure, one skilled in the art may envision variations, modifications, and alternate embodiments falling within the spirit of the broader aspects of the general inventive concept provided in this disclosure that do not depart from the broader scope of the present disclosure.

We claim:

1. A method for determining a matching entity, comprising:
    receiving, at an entity matching system, a request to determine a first entity matching with a second entity;
    parsing the received request to determine demographic fields data related to the second entity;
    comparing the demographic fields data with indexed demographic data of a record;
    determining comparison weight values for a plurality of demographic fields based at least in part on the comparison between the demographic fields data and the indexed demographic data, wherein the determining the comparison weight values comprising:
        assigning an agreement weight value as the comparison weight value for each demographic field for data matches;
        assigning a disagreement weight value as the comparison weight value for each demographic field when the data does not match; and
        assigning a null weight value as the comparison weight value for each demographic field for missing data,
    wherein the determining of the comparison weight values further comprises:
        determining a plurality of comparison weight values to assign to the plurality of demographic fields in a third population which comprises:
            determining a first population comprised of a first set of comparison weight values by randomly selecting the first set of comparison weight values from a larger set of comparison weight values, the first set of comparison weight values including one or more of: a first agreement weight value, a first disagreement weight value, or a first null weight value;
            determining a first population matching confidence value for each of the first set of comparison weight values based on how well each of the first set of comparison weight values provides quality matches;
            determining a second population comprised of a second set of comparison weight values selected from the first set of comparison weight values based at least of the first population matching confidence value for each of the first set of comparison weight values, wherein the second set of comparison weight values is smaller than the first set of comparison weight values;
            creating pairs of comparison weight values from the second set of comparison weight values;
            determining a third population comprising a third set of comparison weight values based on the pairs of comparison weight values from the second population, wherein determining the third population further comprises introducing one or more mutations in the third population;
            determining a third population matching confidence value for each of the third set of comparison weight values; and
        determining the plurality of comparison weight values for each of the plurality of demographic fields in the third population based on the third population matching confidence values for each of the third set of comparison weight values;
        aggregating the plurality of comparison weight values for the plurality of demographic fields to generate an aggregated comparison weight value; and
        determining the first entity matching with the second entity from the record based on the aggregated comparison weight value.

2. The method of claim 1, wherein the third set of comparison weight values is smaller than the second set of comparison weight values.

3. The method of claim 1, wherein determining the first population matching confidence value comprises:
    validating the respective comparison weight value according to one or more matching scenarios.

4. The method of claim 3, wherein at least one of the first record and the second record correspond to the matching scenarios indicating a first set of fields of the plurality of demographic fields that match and a second set of fields of plurality of demographic fields that do not match between the first record and the second record.

5. The method of claim 4, wherein determining the third population matching confidence value further comprises overriding an initially assigned matching confidence value.

6. The method of claim 5, wherein overriding the initially assigned matching confidence comprises overriding a first matching confidence between a first field of the first entity and a second field of the second entity based on the matching scenarios.

7. The method of claim 1, wherein determining the second population comprises:
    comparing the matching confidence of each comparison weight value of the first population of comparison weight values with a first predetermined threshold; and
    determining the second population from the first population of comparison weight values having the matching confidence greater than the first predetermined threshold.

8. The method of claim 1, further comprising determining a first comparison weight value from the first population having a highest matching confidence.

9. The method of claim 1, wherein introducing the one or more mutations in the third population comprises inserting random comparison weight values in the third population.

10. The method of claim 1, wherein the mutations are introduced for a predetermined number of times.

11. A system for determining a matching entity, comprising:
    a processor; and
    a memory storage device including instructions that when executed by the processor are operable to:
        receive, at an entity matching system, a request for a unique identifier associated with an entity;

parse the received request to determine demographic fields data related to the entity;

compare the demographic fields data with indexed demographic data;

determine comparison weight values for a plurality of demographic fields based at least in part on the comparison between the demographic fields data and the indexed demographic data, wherein the determining the comparison weight values comprising:

assign an agreement weight value as the comparison weight value for each demographic field for data matches;

assign a disagreement weight value as the comparison weight value for each demographic field when the data does not match; and assign a null weight value as the comparison weight value for each demographic field for missing data, wherein the determination of the comparison weight values further comprises:

determine a plurality of comparison weight values to assign to the plurality of demographic fields in a third population which comprises:

determine a first population comprised of a first set of comparison weight values by randomly selecting the first set of comparison weight values from a larger set of comparison weight values, the first set of comparison weight values including one or more of: a first agreement weight value, a first disagreement weight value, or a first null weight value;

determine a first population matching confidence value for each of the first set of comparison weight values based on how well each of the first set of comparison weight values provides quality matches;

determine a second population comprised of a second set of comparison weight values selected from the first set of comparison weight values based at least of the first population matching confidence value for each of the first set of comparison weight values, wherein the second set of comparison weight values is smaller than the first set of comparison weight values;

creating pairs of comparison weight values from the second set of comparison weight values;

determine a third population comprising a third set of comparison weight values based on the pairs of comparison weight values from the second population, wherein determining the third population further comprises introducing one or more mutations in the third population;

determine a third population matching confidence value for each of the third set of comparison weight values; and aggregate the plurality of comparison weight values for the plurality of demographic fields to generate an aggregated comparison weight value; and determine the unique identifier corresponding to another entity from the indexed demographic data matching with the entity based on the aggregated comparison weight value.

12. The system of claim 11, wherein the second set of comparison weight values is smaller than the first set of comparison weight values, and the third set of comparison weight values is smaller than the second set of comparison weight values.

13. The system of claim 12, further comprising an index comprising the indexed demographic data for entities, wherein each entity of the entities is associated with an assigned unique identifier.

14. The system of claim 13, wherein the indexed demographic data comprises one or more indexed demographic fields with one or more values that are associated with the entities.

15. The system of claim 11, wherein the instructions are further operable to override the matching confidence.

16. A computer readable storage device including computer readable instructions, which when executed by a processing unit perform a method including:

receiving, at an entity matching system, a request for a unique identifier associated with an entity;

parsing the received request to determine demographic fields data related to the entity;

determining comparison weight values for a plurality of demographic fields based at least in part on the comparison between the demographic fields data and the indexed demographic data, wherein the determining the comparison weight values comprising:

assigning an agreement weight value as the comparison weight value for each demographic field for data matches;

assigning a disagreement weight value as the comparison weight value for each demographic field when the data does not match; and assigning a null weight value as the comparison weight value for each demographic field for missing data, wherein the determining of the comparison weight values further comprises:

determining a plurality of comparison weight values to assign to the plurality of demographic fields in a third population which comprises:

determining a first population comprised of a first set of comparison weight values by randomly selecting the first set of comparison weight values from a larger set of comparison weight values, the first set of comparison weight values including one or more of: a first agreement weight value, a first disagreement weight value, or a first null weight value;

determining a first population matching confidence value for each of the first set of comparison weight values based on how well each of the first set of comparison weight values provides quality matches;

determining a second population comprised of a second set of comparison weight values selected from the first set of comparison weight values based at least of the first population matching confidence value for each of the first set of comparison weight values, wherein the second set of comparison weight values is smaller than the first set of comparison weight values;

creating pairs of comparison weight values from the second set of comparison weight values;

determining a third population comprising a third set of comparison weight values based on the pairs of comparison weight values from the second population, wherein determining the third population further comprises introducing one or more mutations in the third population;

determining a third population matching confidence value for each of the third set of comparison weight values; and aggregating the plurality of comparison weight values for the plurality of demographic fields to generate an aggregated comparison weight value; and determining the first entity matching the second entity from the record based on the aggregated comparison weight value.

17. The computer readable storage device of claim 16, wherein the third set of comparison weight values is smaller than the second set of comparison weight values.

18. The computer readable storage device of claim 16, wherein determining the first population matching confidence value comprises:

validating the respective comparison weight value according to one or more matching scenarios.

19. The computer readable storage device of claim 16, wherein determining the third population matching confidence value further comprises overriding an initially assigned matching confidence value.

20. The computer readable storage device of claim 16, wherein the mutations are introduced for a predetermined number of times.

\* \* \* \* \*